US008021436B2

(12) United States Patent
Lant et al.

(10) Patent No.: US 8,021,436 B2
(45) Date of Patent: Sep. 20, 2011

(54) CLEANING AND/OR TREATMENT COMPOSITIONS COMPRISING A XYLOGLUCAN CONJUGATE

(75) Inventors: Neil Joseph Lant, Newcastle Upon Tyne (GB); Lars Olof Anderson, Malmoe (SE)

(73) Assignee: The Procter & Gamble Company, Cincinnati, OH (US)

( * ) Notice: Subject to any disclaimer, the term of this patent is extended or adjusted under 35 U.S.C. 154(b) by 308 days.

(21) Appl. No.: 12/284,077

(22) Filed: Sep. 18, 2008

(65) Prior Publication Data

US 2009/0088362 A1 Apr. 2, 2009

Related U.S. Application Data

(60) Provisional application No. 60/995,643, filed on Sep. 27, 2007.

(51) Int. Cl.

| | |
|---|---|
| ***C11D 3/22*** | (2006.01) |
| ***C11D 1/00*** | (2006.01) |
| ***A61K 8/73*** | (2006.01) |
| ***B08B 3/04*** | (2006.01) |

(52) U.S. Cl. .......... 8/137; 510/470; 510/474; 424/70.13

(58) Field of Classification Search .................. 510/470, 510/474; 424/70.13; 8/137

See application file for complete search history.

(56) References Cited

U.S. PATENT DOCUMENTS

| | | | | |
|---|---|---|---|---|
| 4,430,243 | A | 2/1984 | Bragg | |
| 4,597,898 | A | 7/1986 | Vander Meer | |
| 4,760,025 | A | 7/1988 | Estell et al. | |
| 4,762,636 | A | 8/1988 | Balliello et al. | |
| 4,990,280 | A | 2/1991 | Thorengaard et al. | |
| 5,486,303 | A | 1/1996 | Capeci et al. | |
| 5,489,392 | A | 2/1996 | Capeci et al. | |
| 5,516,448 | A | 5/1996 | Capeci et al. | |
| 5,565,422 | A | 10/1996 | Del Greco et al. | |
| 5,569,645 | A | 10/1996 | Dinniwell et al. | |
| 5,574,005 | A | 11/1996 | Welch et al. | |
| 5,576,282 | A | 11/1996 | Miracle et al. | |
| 5,595,967 | A | 1/1997 | Miracle et al. | |
| 5,597,936 | A | 1/1997 | Perkins et al. | |
| 5,691,297 | A | 11/1997 | Nassano et al. | |
| 5,879,584 | A | 3/1999 | Bianchetti et al. | |
| 6,020,303 | A | 2/2000 | Cripe et al. | |
| 6,060,443 | A | 5/2000 | Cripe et al. | |
| 6,225,462 | B1 * | 5/2001 | Berry et al. | 536/123.1 |
| 6,225,464 | B1 | 5/2001 | Hiler, II et al. | |
| 6,291,412 | B1 | 9/2001 | Kvita et al. | |
| 6,306,812 | B1 | 10/2001 | Perkins et al. | |
| 6,312,936 | B1 | 11/2001 | Poulose et al. | |
| 6,326,348 | B1 | 12/2001 | Vinson et al. | |
| 2003/0087790 | A1 | 5/2003 | Puelle Andrade et al. | |
| 2003/0087791 | A1 | 5/2003 | Bonelli et al. | |
| 2004/0048764 | A1 | 3/2004 | Kim et al. | |
| 2004/0091977 | A1 | 5/2004 | Teeri et al. | |
| 2005/0003983 | A1 | 1/2005 | Kim et al. | |
| 2005/0227891 | A1 | 10/2005 | Dreyer et al. | |
| 2006/0111264 | A1 | 5/2006 | Smets et al. | |
| 2006/0242770 | A1 | 11/2006 | Albersheim et al. | |

FOREIGN PATENT DOCUMENTS

| | | | |
|---|---|---|---|
| EP | 1070115 | B1 | 3/2008 |
| WO | WO 95/34628 | * | 12/1995 |
| WO | WO 98/17767 | A1 | 4/1998 |
| WO | WO 00/32601 | A2 | 6/2000 |
| WO | WO 01/05874 | A1 | 1/2001 |
| WO | WO 2004/094646 | * | 11/2004 |
| WO | WO 2005/042532 | A1 | 5/2005 |

OTHER PUBLICATIONS

Brumer III, Harry, et al., Activation of Crystalline Cellulose Surfaces through the Chemoenzymatic Modification of Xyloglucan, Journal of the American Chemical Society, 2004, pp. 5715-5721, vol. 126.

Gustavsson, Malin T., et al., Modification of Cellulose Fiber Surfaces by Use of a Lipase and a Xyloglucan Endotransglycosylase, Biomacromolecules, 2005, pp. 196-203, vol. 6.

Shaath, Nadim A., Evolution of Modern Sunscreen Chemicals KATO Worldwide, Ltd./ Nickstadt-Moeller, Mt. Vernon, New York, pp. 3-33.

Lowe, Nicholas J. (Ed.), et al., Sunscreens Development, Evaluation, and Regulatory Aspects, Cosmetic Science and Technology Series, 2nd Edition, vol. 15.

Shaath, Nadim A., Encyclopedia of UV Absorbers for Sunscreen Products, Cosmetics & Toiletries, Mar. 1987, pp. 21-39, vol. 102.

Risch, Sara J. (Ed.), et al., Encapsulation and Controlled Release of Food Ingredients, ACS Symposium Series 590,Washington, D.C., 1995.

* cited by examiner

*Primary Examiner* — Brian P Mruk

(74) *Attorney, Agent, or Firm* — Melissa G Krasovec; James F McBride; Leonard W Lewis

(57) ABSTRACT

This invention relates to compositions comprising a xyloglucan conjugate and processes for making and using such compositions including the use of such compositions to clean and/or treat a situs.

8 Claims, No Drawings

CLEANING AND/OR TREATMENT COMPOSITIONS COMPRISING A XYLOGLUCAN CONJUGATE

CROSS-REFERENCES TO RELATED APPLICATIONS

This application claims priority under 35 U.S.C. §119(e) to U.S. Provisional Application Ser. No. 60/995,643 filed Sep. 27, 2007.

FIELD OF INVENTION

Compositions comprising a xyloglucan conjugate and processes for making and using such compositions.

BACKGROUND OF THE INVENTION

Polysaccharide-conjugates can be used to deliver materials, such as benefit agents, to a situs. Generally, a benefit agent constitutes the aforementioned conjugate portion of a polysaccharide conjugate. Unfortunately, when such polysaccharide conjugates are employed in a cleaning or treatment context, they are incompatible with other cleaning and/or treatment ingredients, the deposition of such polysaccharide conjugates on the target situs is not as great as desired and, in many cases, the color of the situs is negatively impacted by such deposition. In addition, the use of such polysaccharide conjugates is not economical as the processes employed to produce such polysaccharide conjugates are not as efficient as desired and/or do not allow for all the desired conjugates to be linked to the polysaccharide. Thus, the use of this technology continues to be limited.

Surprisingly, when select xyloglucan conjugates are employed in cleaning and/or treatment compositions, the aforementioned problems are eliminated or greatly reduced.

SUMMARY OF THE INVENTION

This invention relates to compositions comprising a xyloglucan conjugate and processes for making and using such compositions.

DETAILED DESCRIPTION OF THE INVENTION

Definitions

As used herein, the term "cleaning and/or treatment composition" includes, unless otherwise indicated, granular or powder-form all-purpose or "heavy-duty" washing agents, especially laundry detergents; liquid, gel or paste-form all-purpose washing agents, especially the so-called heavy-duty liquid types; liquid fine-fabric detergents; fabric rejuvenation products designed to restore the appearance of faded fabrics; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, laundry bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the phrase "is independently selected from the group consisting of . . . " means that moieties or elements that are selected from the referenced Markush group can be the same, can be different or any mixture of elements.

As used herein, the articles "a" and "an" when used in a claim, are understood to mean one or more of what is claimed or described.

As used herein, the terms "include", "includes" and "including" are meant to be non-limiting.

Unless otherwise noted, all component or composition levels are in reference to the active level of that component or composition, and are exclusive of impurities, for example, residual solvents or by-products, which may be present in commercially available sources.

Unless otherwise noted, the enzymes of the present invention are expressed in terms of active protein level and are exclusive of impurities, for example, residual solvents or by-products, which may be present in commercially available sources.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Xyloglucan Conjugate

Suitable xyloglucan conjugates include xyloglucan conjugates that are conjugated at their reducing end with a benefit agent. Suitable non-limiting examples of xyloglucan conjugates may be represented by one of the structures below, based on a ring-opened terminal glucose moiety at the reducing end of a xyloglucan oligosaccharide and/or polysaccharide:

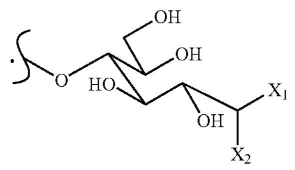

wherein,

∫ represents the remainder of the xyloglucan oligosaccharide or polysaccharide; and $X_1$ and $X_2$ represent chemical groups selected from

—H;

—$R_1$;

-$(L_1)$-$R_1$;

—NH—$(L_1)$—$R_1$;

—S—$(L_1)$—$R_1$

—O—$(L_1)$—$R_1$;

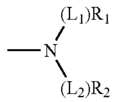

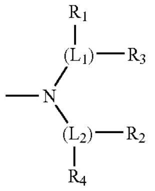

=O

Wherein a maximum of one of the groups $X_1$ and $X_2$ is —H and $L_1$ and $L_2$ represent optional covalently bonded linker group(s) selected from the following:

—C(=O)—
—C(=S)—
—$SO_2$—
-Alk-
—Ar—
—Ar-Alk-
-Alk-
-Alk-Ar—
-Alk-Ar-Alk-
—Ar-Alk-Ar—

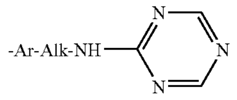

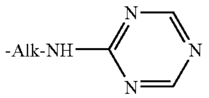

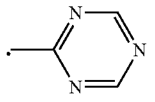

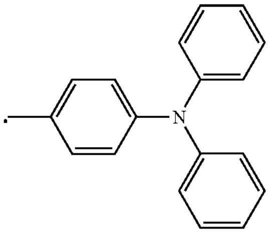

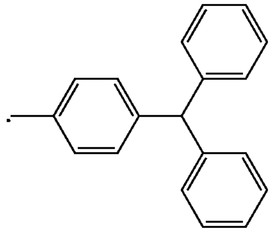

Wherein Ar is an aryl or naphthyl ring, which may be further substituted. Alk is an aliphatic group which may be further substituted.

$R_1$, $R_2$, $R_3$, and $R_4$ represent covalently bonded benefit group(s).

Suitable xyloglucan conjugates can be produced in accordance with the teachings of USPA 2004/0091977 A1 and USPA 2006/0242770 A1, and H. Brumer et al., Journal of the American Chemical Society, 2004, volume 126, p. 5715-5721.

In one aspect, in addition to reducing end conjugation, the xyloglucan oligosaccharides or polysaccharides are conjugated at their beta-1,4-linked glucan backbone or side chains.

In one aspect, side chain conjugation can be accomplished by treatment of xyloglucan with galactose oxidase, which oxidizes galactose side chain residues to aldehydes which can then be reacted with amine-containing benefit groups to produce an imine-linked covalent conjugate.

In one aspect, vicinal diol functionality present throughout the xyloglucan backbone and side chains can be derivatised by treatment with cyanogen bromide which leads to a cyclic imidocarbonate or cyanate ester intermediate which can be reacted with amine-containing benefit groups to produce a covalent conjugate linked through an isourea, N-substituted imidocarbonate, or N-substituted carbamate.

In one aspect, primary hydroxyl groups present on unsubstituted glucose residues in the backbone and in side chain residues can be acylated using lipase as a catalyst and further derivatised in accordance with M. T. Gustavsson et al., Biomacromolecules, 2005, volume 6, pp 196-203.

In one aspect, any of the xyloglucan conjugates disclosed in the present specification can be processed into particulates. Without being bound by theory, it is believed that such particulates have enhanced stability and/or solubility. In one aspect, said particulates may be encapsulates. The encapsulating material typically encapsulates at least part, and normally all, of the xyloglucan conjugate. Typically, the encapsulating material is water-soluble and/or water-dispersible. The encapsulating material may be a microsphere made from plastic such as thermoplastics, acrylonitrile, methacrylonitiile, polyacrylonitrile, polymethacrylonitrile and mixtures thereof; commercially available microspheres that can be used are those supplied by Expancel of Stockviksverken, Sweden under the trademark Expancel®, and those supplied by PQ Corp. of Valley Forge, Pa. USA under the product codes PM 6545, PM 6550, PM 7220, PM 7228, and tradenames Extendospheres®, Luxsil®, Q-cel® and Sphericel®.

In one aspect, said particulates may be "noodles", used to refer to generally cylindrical particles prepared by extruding a paste through the holes of extruder die plate followed by processing the extrudates into pieces of desirable length.

In one aspect, said particulates may be spray dried granules, produced by spray drying the xyloglucan conjugate with other materials to produce particulates with the desired properties.

In one aspect, said particulates may be agglomerates produced by granulating the xyloglucan conjugate with other materials to produce particulates with the desired properties.

Partially purified xyloglucan polysaccharide is available from Dainippon Pharmaceuticals, Osaka, Japan under the tradename Glyoid® S such material is generally suitable for use as a raw material for the synthesis of xyloglucan conjugates. Where further purification is desired, such purification can be accomplished by dispersing the starting material in cold deionised water, while stirring for 12 hours so as to obtain a homogeneous dispersion. In order to separate, by precipitation, any possible proteins present, the dispersion so obtained is heated for 30 minutes at 80° C., and, after cooling, is subjected to centrifugation for 30 minutes at 5000 r.p.m. The supernatant solution is then dialysed against water for at least 48 hours at 4° C., using 12,000-14,000 daltons cut-off membranes. The resulting solution is finally lyophilised, giving a translucid, white final product that is typically totally soluble in water. The absence of contaminating proteins can be verified by polyacrylamide gel electrophoresis with sodium dodecyl sulphate (SDS-PAGE).

Xyloglucan has a backbone composed of 1,4-linked β-D-Glcp residues. Up to 75% of these residues are substituted at O6 with mono-, di-, or triglycosyl side chains. A single letter nomenclature is used to simplify the naming of xyloglucan side chain structures. For example, a capital G represents a unbranched Glcp residue. A capital F represents a Glcp residue that is substituted with a fucose-containing trisaccharide. The nomenclature is shown below:

G = -4)-β-D-Glcp-(1-

X = α-D-Xylp-(1-6)-β-D-Glcp-(1-
4

L = β-D-Galp-(1-2)-α-D-Xylp-(1-6)-β-D-Glcp-(1-
4

F = α-L-Fucp-(1-2)-β-D-Galp(1-2)-α-D-Xylp-(1-6)-β-D-Glcp-(1-
4

S = α-L-Araf-(1-2)-α-D-Xylp-(1-6)-β-D-Glcp-(1-
4

T = α-L-Araf-(1-3)-α-L-Araf-(1-2)-a-D-Xylp-(1-6)-β-D-Glcp-(1-
4

J = α-L-Galp-(1,2)-β-D-Galp-(1-2)-α-D-Xylp-(1-6)-β-D-Glcp-(1-
4

Xyloglucans may be classified as XXXG-type of XXGG-type. XXXG have three consecutive backbone residues that are substituted with Xylp and a fourth unbranched backbone residue. XXGG xyloglucans have two consecutive branched backbone residues and two unbranched backbone residues.

The xyloglucan conjugates of the present invention and compositions comprising same can deliver a diversity of desired benefits to fabrics including, but not limited to, improved fabric odor, stain removal, soil release, soil repellency, cleaning, whitening, dyeing, tinting, resistance to dye fading, softening, improved hand, resistance to pilling, resistance to wrinkling, ease of ironing, transfer of materials to human skin, resistance to abrasion, retention of fabric shape, improved fabric tensile strength, protection from microbial buildup, protection from attack by fungi or insects and/or reduced skin irritation.

Suitable conjugated benefit groups, denoted as R, may be linked to the ring-opened xyloglucan oligosaccharide or polysaccharide, either directly, for example through an amide or ester bond, or through a linker group. A linker group may be useful when it is desired to join chemical entities which might not otherwise interact, for example due to lack of chemical reactivity, some other form of chemical incompatibility or steric hindrance. A linker group may also be useful when it is desired to conjugate a single xyloglucan oligosaccharide reducing end with more than one benefit group.

Prior to linking the benefit group R with the xyloglucan, the benefit group R typically contains a moiety selected from the group consisting of amine, alcohol, aldehyde, ketone, carboxylic acid, sulfonic acid, thiol, acyl halide, alkene, nitro compound, diazonium ion, alkyl halide, alkyl toluenesulfonate and mixtures there of. Typically, the benefit group R and the xyloglucan are linked (conjugated) via a linker group including, but are not limited to, amide, azo compound, carbonate, disulfide, ether, ester, hydroperoxide, imine, imide, nitrate, phosphodiester, phosphate, sulfide, sulfone, ketone, urethane, thioester, triazine and/or sulfonamide functional groups.

In one aspect of the invention, the benefit group is linked to the xyloglucan oligosaccharide or polysaccharide through a bond which may be subsequently hydrolysed during the washing or drying stages of the wash process. In one aspect, such hydrolysis may be catalysed by a hydrolase enzyme including, but not limited to, a lipase, esterase, cutinase, amidase and mixtures there of.

Suitable conjugated benefit groups R include, but are not limited to, perfumes, perfume particles, enzymes, fluorescent brighteners, oil repellent agents, water repellent agents, soil release agents, soil repellent agents, dyes including fabric renewing dyes, hueing dyes, dye intermediates, dye fixatives, lubricants, fabric softeners, photofading inhibitors, anti-wrinkle/ironing agents, shape retention agents, UV absorbers, sunscreens, antioxidants, crease resistant agents, antimicrobial agents, skin benefit agents, anti-fungal agents, insect repellents, photobleaches, photoinitiators, sensates, enzyme inhibitors, bleach catalysts, odor neutralizing agents, pheromones and mixtures there of.

Examples of suitable perfume groups include acetyl cedrene, 4-acetoxy-3-pentyltetrahydropyran, 4-acetyl-6-t-butyl-1,1-dimetylindane, available under the trademark Celestolide®, 5-acetyl-1,1,2,3,3,6-hexamethyl indane, available under the trademark Phantolide®, 6-acetyl-1-isopropyl-2,3,3,5-tetramethylindane, available under the trademark Traseolide®, alpha-n-amylcinnamic aldehyde, amyl salicylate, aubepine, aubepine nitrile, aurantion, 2-t-butylcyclohexyl acetate, 2-t-butylcyclohexanol, 3-(p-t-butylphenyl) propanal, 4-t-butylcyclohexyl acetate, 4-t-butyl-3,5-dinitro-2,6-dimethyl acetophenone, 4-t-butylcyclohexanol, benzoin siam resinoids, benzyl benzoate, benzyl acetate, benzyl propionate, benzyl salicylate, benzyl isoamyi ether, benzyl alcohol, bergamot oil, bornyl acetate, butyl salicylate, carvacrol, cedar atlas oil, cedryl methyl ether, cedryl acetate, cinnamic alcohol, cinnamyi propionate, cis-3-hexenol, cis-3-hexenyl salicylate, citronella oil, citronellol, citronellonitrile, citronellyl acetate, citronellyloxyacetaldehyde, cloveleaf oil, coumarin, 9-decen-1-ol, n-decanal, n-dodecanal, decanol, decyl acetate, diethyl phthalate, dihydromyrcenol, dihydromyrcenyl formate, dihydromyrcenyl acetate, dihydroterpinyl acetate, dimethylbenzyl carbinyl acetate, dimethyibenzyicarbinol, dimethylheptanol, dimethyloctanol, dimyrcetol, diphenyl oxide, ethyl naphthyl ether, ethyl vanillin, ethylene brassylate, eugenol, florocyclene, geraniol, geranium oil, geranonitrile, geranyl nitrile, geranyl acetate, 1,1,2,4,4,7-hexamethyi-6-acetyl-1,2,3,4-tetrahydronaphthalene, available under the trademark Tonalid®, 1,3,4,6,7,8-hexahydro-4,6,6,7,8,8-hexamethylcyclopenta-2-benzopyran, available under the trade mark Galaxolide®, 2-n-heptylcyclopentanone, 3a,4,5,6,7,7a-hexahydro-4,7-methanol(3)H-inden-6-yl-propionate, available under the trademark Florocyclene®, 3a-4,5,6,7,7a-hexahydro-4,7-methano-1(3)H-inden-6-ylacetate, available under the trademark Jasmacyclene®, 4-(4'-hydroxy-4'-methylpentyl)-3-cyclo hexenecarbaldehyde, alpha-hexylcinnamic aldehyde, heliotropin, Hercolyn D, hexyl aldone, hexyl cinnamic aldehyde, hexyl salicylate, hydroxycitronellal, i-nonyl formate, 3-isocamphylcyclohexanol, 4-isopropylcyclohexanol, 4-isopropylcyclohexyl methanol, indole, ionones, irones, isoamyl salicylate, isoborneol, isobornyl acetate, isobutyl salicylate, isobutylbenzoate, isobutylphenyl acetate, isoeugenol, isolongifolanone, isomethyl ionones, isononanol, isononyl acetate, isopulegol, lavandin oil, lemongrass oil, linalool, linalyl acetate, LRG 201, 1-menthol, 2-methyl-3-(p-isopropyl phenyl)propanal, 2-methyl-3-(p-t-butyl phenyl)propanal, 3-methyl-2-pentyl-cyclopentanone, 3-methyl-5-phenyl-pentanol, alpha and beta methyl naphthyl ketones, methyl ionones, methyl dihydrojasmonate, methyl naphthyl ether, methyl 4-propyl phenyl ether, Mousse de chene Yugo, Musk ambrette, myrtenol, neroli oil, nonanediol-1,3-diacetate, nonanol, nonanolide-1,4, nopol acetate, 1,2,3,4,5,6,7,8-octahydro-2,3, 8,8-tetramethyl-2-acetyl-naphthalene, available under the trademark Iso-E-Super®, octanol, Oppoponax resinoid, orange oil, p-t-amyl cyclohexanone, p-t-butylmethylhydrocinnamic aldehyde, 2-phenylethanol, 2-phenylethyl acetate, 2-phenylpropanol, 3-phenylpropanol, para-menthan-7-ol, para-t-butyl phenyl methyl ether, patchouli oil, pelargene, petitgrain oil, phenoxyethyl isobutyrate, phenylacetaidehyde diethyl acetal, phenyl acetaidehyde dimethyl acetal, phenylethyl n-butyl ether, phenylethyl isoarnyl ether, phenyl ethyl phenyl acetate, pimento leaf oil, rose-d-oxide, Sandalone, styrally]acetate, 1,1,4,4-tetramethyl-6-acetyl-7ethyl-1,2,3,4-tetrahydronaphthalene, available under the trademark Versalide®, 3,3,5-trimethyl hexyl acetate, 3,5,5-trimethylcyclohexanol, terpineol, terpinyl acetate, tetrahydrogeraniol,

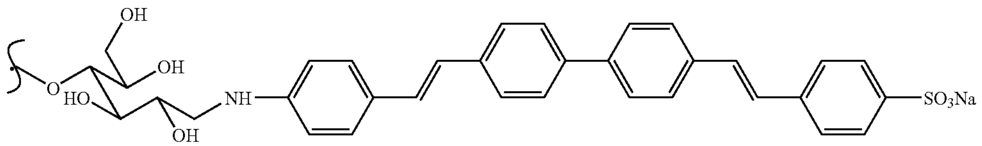

tetrahydrolinalool, tetrahydromuguol, tetra hydromyrcenol, thyme oil, trichloromethylphenylcarbinyl acetate, tricyclodecenyl acetate, tricyclodecenyl propionate, 10-undecen-1-al, gamma undecalactone, 10-undecen-1-ol, undecanol, vanillin, vetiverol, vetiveryl acetate, vetyvert oil, acetate and propionate esters of alcohol in the list above, aromatic nitromusk fragrances, indane musk fragrances, isochroman musk fragrances, macrocyclic ketones, macrolactone musk fragrances, tetralin musk fragrances and mixtures there of. An example of a xyloglucan delta-damascone conjugate, suitable for use as a properfume in laundry treatment compositions to achieve dry fabric odor benefits, is given below.

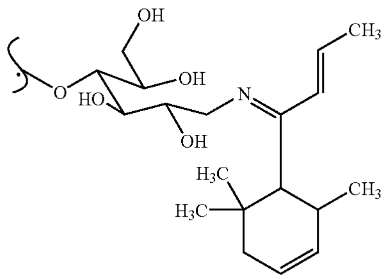

Examples of suitable perfume particles include perfume encapsulates. Encapsulation techniques suitable for production of perfume encapsulates are given in S. J. Risch, G. A. Reineccius (Ed), "Encapsulation and controlled release of food ingredients", ACS symposium series 590, Washington D.C., 1995. Suitable encapsulating materials include starches, poly(vinylacetate), melamine/formaldehyde condensates and urea/formaldehyde condensates.

Examples of suitable enzymes include protease, amylase, beta-glucanase, lipase, hemi-cellulase, cutinase, pectate lyase, pectin lyase, rhamnogalacturonan lyase, endo-1,4-galactanase, xylanase, arabinanase, alpha-L-7-arabinofuranosidase, mannan endo-1,4-mannosidase, beta mannosidase, beta-1,3-1,4-glucanase, rhamnogalacturonan hydrolase, exo-polygalacturonase, rhamnogalacturonase, glucan 1,3-beta-glucosidase, glucan endo-1,6-beta-glucosidase, mannan 5 endo-1,4-beta-mannosidase, endo-1,4-beta-xylanase, eellulose 1,4-cellobiosidase, cellobiohydrolase, polygalacturonases, acetyl and methyl esterase enzymes such as: rhamnogalacturonan methyl esterase, rhamnogalacturonan acetyl esterase, pectin methylesterase, pectin acetylesterase, xylan methyl esterase, acetyl xylan esterase, feruloyl esterase, cinnamoyl esterase and mixtures there of.

Examples of suitable fluorescent brighteners include C.I. Fluorescent Brighteners 1 through 396, and those belonging to the classes of diaminostilbene sulfonic acid derivatives, diarylpyrazoline derivatives, bisphenyl-distyryl derivatives and mixtures thereof. An example of a xyloglucan conjugate with fluorescent brightener group, suitable for improving the whiteness perception of laundered fabrics as part of laundry treatment compositions, is given below.

Examples of suitable oil, water or soil repellent agents include silicone derivatives; fluoropolymers; perfluoro $C_8$-$C_{18}$ alkylamines; perfluoro $C_8$-$C_{18}$ carboxylic acids; olefinic/acrylic polymers comprising a combination of alpha, beta unsaturated carboxylated monomers, and olefinic monomers such as styrene, alpha methyl styrene ("AMS") or blocked alpha, beta unsaturated esterified carboxylates or amides; carboxylated polymer salts; low molecular weight carboxylated water soluble polymers (below molecular weight of 10,000) which may or may not contain some sulfonated material such as sulfonated castor oil, or formaldehyde/sulfonated phenol condensate, for example Zelan® 338 EI Dupont de Nemours Co. of Wilmington, Del., USA, Fluorad® FC-661 and FIK-657 from the 3M Company of Maplewood, Minn., USA.

Examples of suitable dyes include C.I. Acid Yellow 1 through 262, C.I. Acid Orange 1 through 181, C.I. Acid Red 1 through 449, C.I. Acid Violet 1 through 313, C.I. Acid Blue 1 through 360, C.I. Acid Green 1 through 125, C.I. Acid Brown 1 through 474, C.I. Acid Black 1 through 244, C.I. Basic Yellow 1 through 108, C.I. Basic Orange 1 through 69, C.I. Basic Red 1 through 118, C.I. Basic Violet 1 through 51, C.I. Basic Blue 1 through 161, C.I. Basic Green 1 through 16, C.I. Basic Brown 1 through 23, C.I. Basic Black 1 through 11, C.I. Direct Yellow 1 through 177, C.I. Direct Orange 1 through 122, C.I. Direct Red 1 through 277, C.I. Direct Violet 1 through 110, C.I. Direct Blue 1 through 314, C.I. Direct Green 1 through 105, C.I. Direct Brown 1 through 250, C.I. Direct Black 1 through 204, C.I. Reactive Yellow 1 through 213, C.I. Reactive Orange 1 through 139, C.I. Reactive Red 1 through 283, C.I. Reactive Violet 1 through 47, C.I. Reactive Blue 1 through 274, C.I. Reactive Green 1 through 33, C.I. Reactive Brown 1 through 50, C.I. Reactive Black 1 through 51 and mixtures and analogues there of. An example of a xyloglucan fabric hueing dye conjugate, suitable for improving the whiteness perception of laundered fabrics as part of fabric treatment compositions is given below.

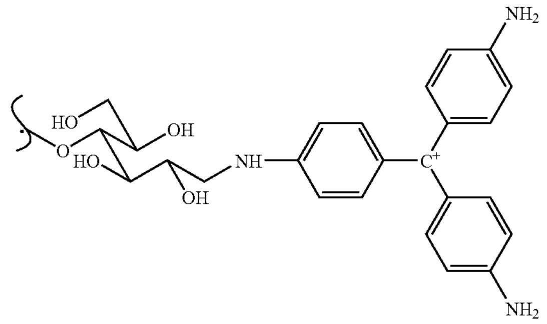

An example of a xyloglucan black dye conjugate, suitable for use in laundry treatment compositions designed to rejuvenate the appearance of faded black fabrics, is given below:

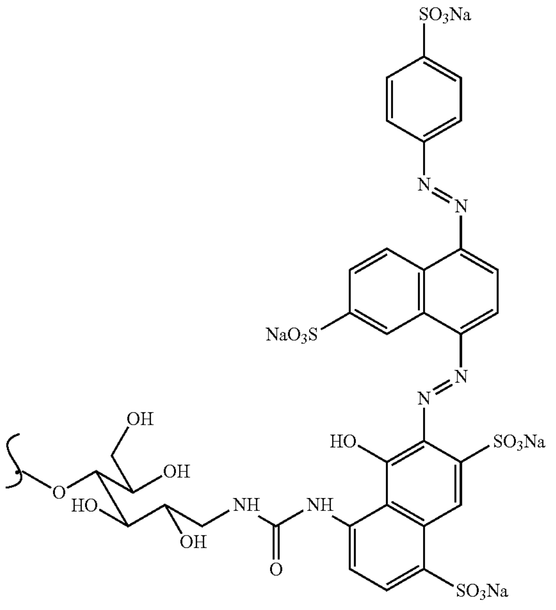

Examples of suitable dye intermediates include 8-amino-1-naphthol-3,6-disulfonic acid (H-acid), 4,4'-Diamino Benzo Sulphon Aniline (DASA), Gama acid, Broenners acid, Meta Phenylene diamine 4, Sulphonic Acid (MPDSA), 3,3'-dichlorobenzaldazine (DCB).

Examples of suitable lubricants include silicones, waxes and sugar polyesters such as sucrose polyesters, glucose polyesters and cellobiose polyesters.

Examples of suitable fabric softeners include alkyl-modified quaternary ammonium compounds such as diester quaternary ammonium compounds (DEQA); polyquaternary ammonium compounds; triethanolamine esterified with carboxylic acid and quaternized (so called "esterquat"), amino esterquats, cationic diesters, betaine esters, betaines, silicone or silicone emulsions comprising aminosilicones, cationic silicones, quat/silicone mixtures, functionalized polydimethyl siloxane and mixtures thereof.

Examples of suitable photofading inhibitors include UV absorbers. Suitable molecules typically have an extinction co-efficient greater than 2000 l $mol^{-1}$ $cm^{-1}$ at a wavelength of maximal absorption. Typically, suitable UV absorbers have a maximal absorption at wavelengths of from about 290 to about 370 nm, from about 310 to about 350 nm, or even from about 330 to about 350 nm. Examples of UV absorbers, listed as sunscreens, are given in Cosmetic Science and Technology Series, Vol. 15; Sunscreens; 2nd edition; edited by Lowe, Shoath and Pathak; Cosmetics and Toiletries; Vol. 102; March 1987—pages 21-39; and Evolution of Modern Sunscreen Chemicals; pages 3-35 both by N. A. Saarth. Suitable UV absorbers include, but are not limited to, compounds active through non-radiative deactivation; derivatives of benzophenone with substituents in the 2- and/or 4-position; substituted benzotriazoles, for example, water-soluble benzenesulfonic acid-3-(2H-benzotriazol-2-yl)-4-hydroxy-5-(methylpropyl)-monosodium salt (Cibafast® H); acrylates phenyl-substituted in the 3-position (cinnamic acid derivatives), optionally with cyano groups in the 2-position; salicylates; organic Ni complexes; umbelliferone; endogenous urocanic acid and mixtures there of. In one aspect, biphenyl derivatives, stilbene derivatives and mixtures thereof are useful. Stilbene derivatives are commercially available from Ciba Specialty Chemicals of Basel, Switzerland as Tinosorb® FD or Tinosorb® FR. Suitable UV-B absorbers, include, but are not limited to, camphor derivatives including 3-benzylidenecamphor, 3-(4-methylbenzylidene)camphor, 3-benzylidene-norcamphor and mixtures thereof; 4-aminobenzoic acid derivatives, including 4.(dimethylamino)benzoic acid 2-ethylhexyl ester, 4-(dimethylamino)benzoic acid 2-octyl ester, 4-(dimethylamino)benzoic acid amyl ester and mixtures thereof; esters of cinnamic acid, including 4-methoxycinnamic acid 2-ethylhexyl ester, 4-methoxycinnamic acid propyl ester, 4-methoxycinnamic acid isoamyl ester, 2-cyano-3,3-phenylcinnamic acid 2-ethylhexyl ester (Octocrylene®) and mixtures thereof; esters of salicylic acid including salicylic acid 2-ethylhexyl ester, salicylic acid 4-isopropylbenzyl ester, salicylic acid homomenthyl ester and mixtures thereof; derivatives of benzophenone, including 2-hydroxy-4-methoxybenzophenone, 2-hydroxy-4-methoxy-4-methylbenzophenone 2,2-dihydroxy-4-methoxy-benzophenone and mixtures there of; esters of benzyalmalonic acid, including 4-methoxybenzylmalonic acid di-2-ethylhexyl ester; triazine derivatives including, 2,4,6-trianilino-(p-carbo-2-ethyl-1-hexyloxy)-1,3,5-triazine, octyl triazone, dioctyl butamido triazone (Uvasorb® HEB) and mixtures there of; propane-1,3-diones including 1-(4-tert-butylphenyl)-3-(4-methoxyphenyl)propane-1,3-dione; ketotricyclo-(5.2.1.0)decane derivatives; 2-phenylbenzimidazole-5-sulfonic acid and alkali metal, alkaline earth metal, ammonium, alkylammonium, alkanolammonium and glucammonium salts thereof, sulfonic acid derivatives of benzophenones, for example, 2-hydroxy-4-methoxybenzophenone-5-sulfonic acid and salts thereof sulfonic acid derivatives of 3-benzylidenecamphor, such as for example 4-(2-oxo-3-bornylidenemethyl)benzene-sulfonic acid and 2-methyl-5-(2-oxo-3-bornylidene)sulfonic acid and salts thereof. Typical UV-A filters are in particular derivatives of benzoylmethane, such as for example 1-(4-tert-butyl-phenyl)-3-(4'-methoxyphenyl)propane-1,3-dione, 4-tert-butyl-4'-methoxydibenzoylmethane (Parsol 1789), 1-phenyl-3-(4'-isopropylphenyl)-propane-1,3-dione and also enamine compounds. The UV-A and UV-B filters can of course also be used as mixtures.

Suitable photofading inhibitors of the anti-oxidant type include benzofurans, coumeric acids or derivatives thereof, for example 2-carboxy benzofuran, and bis(p-amino sulfonates, triazine, DABCO derivatives, tocopherol derivatives, tertiary amines and aromatic substituted alcohols eg butylated hydroxytoluene (BHT), Vitamin C (ascorbic acid) and vitamin E.

Examples of suitable agents for antiwrinkle, crease resistance or ease of ironing include fusible elastomers, polyorganosilicones, aminosilicones with sterically hindered functional groups, water-soluble silicone lubricants, and polymeric nanoparticles.

Examples of suitable bleach catalyst agents include those based on complexes of transition metals and zwitterionic or cationic derivatives of dihydroisoquinolinium salts. An example of a suitable xyloglucan bleach catalyst conjugate, suitable for bleaching soils as part of a laundry detergent composition, is given below.

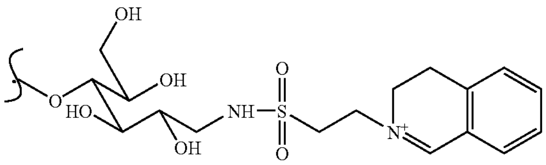

Examples of suitable antimicrobial agents include PCMX (para chlorometa xylenol), triclosan (2,4,4'-trichloro-2'-hydroxy diphenyl ether), 3,4,4'-trichloro carbanilide, and DTBBP (2,t-butyl-4-cyclohexylphenol).

Examples of suitable skin benefit agents include (a) silicone oils, gums and modifications thereof such as linear and cyclic polydimethylsiloxanes, amino, alkyl alkylaryl and aryl silicone oils; (b) fats and oils including natural fats and oils such as jojoba, soybean, rice bran, avocado, almond, olive, sesame, persic, castor, coconut, mink oils; cacao fat, beef tallow, lard; hardened oils obtained by hydrogenating the aforementioned oils; and synthetic mono, di and triglycerides such as myristic acid glyceride and 2-ethylhexanoic acid glyceride; (c) waxes such as carnauba, spermaceti, beeswax, lanolin and derivatives thereof; (d) hydrophobic plant extracts; (e) hydrocarbons such as liquid paraffins, petroleum jelly, microcrystalline wax, ceresin, squalene, and mineral oil; (f) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate for example lauryl lactate, alkyl citrate and alkyl tartrate; is (g) essential oils such as fish oils, mentha, jasmine, camphor, white cedar, bitter orange peel, ryu, turpentine, cinnamon, bergamont, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, pinene, limonene and terpenoid oils; (h) lipids such as cholesterol, ceramides, sucrose esters and pseudo-ceramides (i) vitamins such as A and E, and vitamin alkyl esters, including those vitamin C alkyl esters; (j) sunscreens such as octyl methoxyl cinnamate and butyl methoxy benzoylmethane (Parsol 1789); (k) Phospholipids; and mixtures of any of the foregoing components.

Examples of suitable antifungal agents include 6-acetoxy-2,4-dimethyl-m-dioxane, diiodomethyl-p-tolysulphone, 4,4-dimethyloxazolidine, hexahydro-1,3,5-tris(2-hydroxyethyl)-s-triazine, sodium dimethyldithiocarbamate, sodium 2-mercaptobenzothioazole, zinc dimethyldithiocarbamate, zinc 2-mercaptobenzothiazole, sodium 2-pyridinethiol-1-oxide, sodium 2-pyridinethiol-1-oxide and N-trichloromethylthio-4-cyclohexene-1,2-dicarboximide.

Examples of suitable insect repellents include N-alkyl neoalkanamides wherein the alkyl is of 1 to 4 carbon atoms and the neoalkanoyl moiety is of 7 to 14 carbon atoms, for example, N-methyl neodecanamide; N,N-diethyl meta toluamide (DEET), 2-hydroxyethyl-n-octyl sulphide (MGK 874); N-octyl bicycloheptene dicarboximide (MGK 264); hexahydrodibenzofuran (MGK 11), Di-n-propyl isocinchomerate (MGK 326); 2-Ethyl-1,3-hexanediol, 2-(n-butyl)-2-ethyl-1,3-propanediol, dimethyl phthalate, dibutyl succinate, piperonyl butoxide, pyrethrum, cornmint, peppermint, american spearmint, scotch spearmint, lemon oil, citronella, cedarwood oil, pine oil, limonene, carvone, eucalyptol, linalool, gum camphor, terpineol and fencholic acid.

Examples of suitable photobleaching agents include catalytic photobleaches selected from the group consisting of xanthene dyes including Eosin Y, Phoxine B, Rose Bengal, C.I. Food Red 14 and mixtures thereof, phthalocyanine derivatives including sulfonated zinc phthalocyanine and sulfonated aluminium phthalocyanine. An example xyloglucan conjugate with xanthene photocatalyst group, suitable for delivering stain removal and degerming benefits to fabrics as part of laundry treatment compositions, is given below.

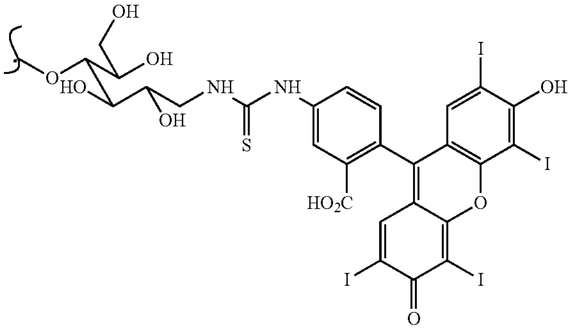

Suitable photo-initiators include photo-initiators selected from the group consisting of aromatic 1,4-quinones such as anthraquinones and naphthaquinones; alpha amino ketones, particularly those containing a benzoyl moiety, otherwise called alpha-amino acetophenones; alphahydroxy ketones, particularly alpha-hydroxy acetophenones; Phosphorus-containing photoinitiators, including monoacyl, bisacyl and trisacyl phosphine oxide and sulphides; dialkoxy acetophenones; alpha-haloacetophenones; trisacyl phosphine oxides; benzoin and benzoin based photoinitiators, and mixtures thereof. In another aspect, suitable photo-initiators include photo-initiators selected from the group consisting of 2-ethyl anthraquinone; Vitamin K3; 2-sulphate-anthraquinone; 2-methyl 1-[4-phenyl]-2-morpholinopropan-1-one (Irgacure® 907); (2-benzyl-2-dimethyl amino-1-(4-morpholinophenyl)-butan-1-one (Irgacure® 369); (1-[4-(2-hydroxyethoxy)-phenyl]-2 hydroxy-2-methyl-1-propan-1-one) (Irgacure® 2959); 1-hydroxy-cyclohexyl-phenyl-ketone (Irgacure® 184); oligo[2-hydroxy 2-methyl-1-[4(1-methyl)-phenyl]propanone (Esacure® KIP 150); 2-4-6-(trimethylbenzoyl)diphenyl-phosphine oxide, bis(2,4,6-trimethylbenzoyl)-phenyl-phosphine oxide (Irgacure® 819); (2,4,6 trimethylbenzoyl)phenyl phosphinic acid ethyl ester (Lucirin® TPO-L); and mixtures thereof.

Examples of suitable sensates include include menthol, methyl lactate, methoneglycerine acetal, cyclohexanol, 5-methyl-2-(1-methylethenyl)-1,2 propanediol, 3-[5-methyl-2-(1-methylethyl)cyclohexyl]-oxy-1,2-propanediol, N,2,3-trimethyl-2-isopropyl butanamide, and N-ethyl-p-menthan-3-carboxamide.

Examples of suitable enzyme inhibitors include lipase inhibitors and cellulase inhibitors.

Examples of suitable odor neutralizing agents include cyclodextrin derivatives.

Examples of suitable pheromones include 16-androstene and estrene steroids.

Suppliers of perfumes include Firmenich, Geneva, Switzerland; International Flavors and Fragrances, New York, N.Y., USA; Givaudan, Vernier, Switzerland; Symrise, Holzminden, Germany. Suppliers of enzymes include Novozymes, Bagsvaerd, Denmark; Genencor, Palo Alto, Calif., USA; AB Enzymes, Darmstadt, Germany. Suppliers of fluorescent brighteners include Ciba Specialty Chemicals, Basel, Switzerland; 3V Sigma, Bergamo, Italy and Paramount Minerals and Chemicals, Mumbai, India. Suppliers of soil/water repellent agents include Wacker Chemie, Munich, Germany; GE Silicones, Fairfield, Conn., USA; Dow Corning, Midland, Mich., USA; Dupont, Wilmington, Del., USA; 3M, Maplewood, Minn., USA; BASF, Ludwigshafen, Germany. Suppliers of fluorescent brighteners include Ciba Specialty Chemicals, Basel, Switzerland; Clariant, Muttenz, Switzerland; BASF, Ludwigshafen, Germany; DyStar, Frankfurt, Germany. Suppliers of lubricants include GE Silicones, Fairfield, Conn., USA; Wacker Chemie, Munich, Germany. Suppliers of UV absorbers and photofading inhibitors include Ciba Specialty Chemicals, Basel, Switzerland; 3V Sigma, Bergamo, Italy; BASF, Ludwigshafen, Germany. Suppliers of antiwrinkle, crease resistance or ease of ironing agents include Wacker Chemie, Munich, Germany; GE Silicones, Fairfield, Conn., USA; Dow Coming, Midland, Mich., USA; Dupont, Wilmington, Del., USA; 3M, Maplewood, Minn., USA; BASF, Ludwigshafen, Germany. Suppliers of bleach catalysts include BASF, Ludwigshafen, Germany; Ciba Specialty Chemicals, Basel, Switzerland. Suppliers of antimicrobial agents include Ciba Specialty Chemicals, Basel, Switzerland Suppliers of skin benefit agents include DSM, Basel, Switzerland; Wacker Chemie, Munich, Germany; Croda, Goole, United Kingdom. Suppliers of antifungal agents include ISP Corporation, Wayne, N.J., USA; Givaudan, Vernier, Switzerland. Suppliers of insect repellents include McLaughlin-Gormley-King Co, Minneapolis, Minn., USA. Suppliers of photobleaching agents include Ciba Specialty Chemicals, Basel, Switzerland. Suppliers of photoinitiators include Ciba Specialty Chemicals, Basel, Switzerland; Lamberti, Gallarate, Italy. Suppliers of sensates include Symrise, Holzminden, Germany. Suppliers of enzyme inhibitors include Aldrich, Milwaukee, Wis., USA. Suppliers of odor neutralizing agents include Wacker Chemie, Munich, Germany. Suppliers of pheromones include Human Pheromone Sciences Inc, Fremont, Calif., USA.

Compositions

In one aspect, a composition comprising a xyloglucan conjugate, conjugated at its reducing end with a benefit agent, and one or more cleaning and/or treatment materials is disclosed. Suitable cleaning and/or treatment materials include, but are not limited to, the adjunct materials listed in the present specification.

In one aspect, the aforementioned composition comprises from about 0.00001% to about 50%, from about 0.0001% to about 10%, from about 0.001% to about 3%, or from about 0.005% to about 1%, or even from about 0.01% to about 0.5% of said xyloglucan conjugate.

In one aspect, the aforementioned composition may comprise any of the xyloglucan conjugates disclosed in the present specification, for example, xyloglucan conjugates with dyes, fluorescent brighteners, perfumes, soil repellent agents or fabric softeners.

In one aspect, the aforementioned composition comprises from about 0.01% to about 99.99999%, from about 0.1% to about 99.9%, from about 0.5% to about 90%, or from about 1% to about 80%, or even from about 5% to about 70% of said one or more cleaning and/or treatment materials.

In one aspect, the aforementioned composition may comprise a carrier or filler. Suitable carriers or fillers include, but are not limited to, sodium sulfate, sodium acetate, sodium chloride, water, talc, dolomite, calcite and clays.

In one aspect, such compositions may be cleaning and/or treatment compositions. Thus it is understood that they may be solids, fluids, soluble pouches containing solids and/or fluids, insoluble capsules containing solids and/or fluids, uncoated or coated tablets, nonwoven sheets impregnated with solid or fluid ingredients.

In one aspect, when said compositions are solids, they may be granular laundry detergents.

In one aspect, when said compositions are solids, they may be tableted laundry detergents coated in a mixture of adipic acid and a cation exchange resin.

In one aspect, when said compositions are fluids, they may be liquid laundry detergents thickened with a shear-thinning structurant.

In one aspect, when said compositions are fluids, they may be liquid fabric rejuvenation compositions.

In one aspect, the aforementioned composition may comprise any combination of material or have any form previously listed.

Adjunct Materials

While not essential for every aspect of the present invention, the non-limiting list of adjuncts illustrated hereinafter are suitable for use in the instant compositions and may be desirably incorporated in certain embodiments of the invention, for example to assist or enhance cleaning performance, for treatment of the substrate to be cleaned, or to modify the aesthetics of the cleaning composition as is the case with perfumes, colorants, dyes or the like. The precise nature of these components, and levels of incorporation thereof, will depend on the physical form of the composition and the nature of the cleaning operation for which it is to be used. Suitable adjunct materials include, but are not limited to, surfactants, builders, polymers, hueing agents, photobleaches, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, solvents, hueing agents, structurants and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to all aspects of Applicants' compositions. Thus, certain embodiments of Applicants' compositions do not contain one or more of the following adjuncts materials: surfactants, builders, polymers, photobleaches, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, solvents, hueing agents, structurants and/or pigments. However, when one or more adjuncts are present, such one or more adjuncts may be present as detailed below:

Bleaching Agents—The cleaning compositions of the present invention may comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) photobleaches (2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxone®, and mixtures thereof. Suitable percarboxylic acids include hydrophobic and hydrophilic peracids having the formula R—(C═O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counter ion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and (4) bleach activators having R—(C═O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Surfactants—The cleaning compositions according to the present invention may comprise a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof. When present, surfactant is typically present at a level of from about 0.1% to about 60%, from about 1% to about 50% or even from about 5% to about 40% by weight of the subject composition.

Builders—The cleaning compositions of the present invention may comprise one or more detergent builders or builder systems. Builders include, but are not limited to, the alkali metal, ammonium and alkanolammonium salts of polyphosphates, alkali metal silicates, alkaline earth and alkali metal carbonates, aluminosilicate builders and polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof.

Chelating Agents—The cleaning compositions herein may contain a chelating agent. Suitable chelating agents include copper, iron and/or manganese chelating agents and mixtures thereof. When a chelating agent is used, the subject composition may comprise from about 0.005% to about 15% or even from about 3.0% to about 10% chelating agent by weight of the subject composition.

Dye Transfer Inhibiting Agents—The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Brighteners—The cleaning compositions of the present invention can also contain components that may tint articles being cleaned, such as fluorescent brighteners. Suitable fluorescent brightener levels include lower levels of from about 0.01, from about 0.05, from about 0.1 or even from about 0.2 wt % to upper levels of 0.5 or even 0.75 wt %.

Dispersants—The compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Enzymes—The cleaning compositions can comprise one or more enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, glucanases, arabinosidases, hyaluronidase, chondroitinase, laccase, amylases, or mixtures thereof. A typical combination is an enzyme cocktail that may comprise, for example, a protease and lipase in conjunction with amylase. When present in a cleaning composition, the aforementioned enzymes may be present at levels from about 0.00001% to about 2%, from about 0.0001% to about 1% or even from about 0.001% to about 0.5% enzyme protein by weight of the composition.

Enzyme Stabilizers—Enzymes for use in detergents can be stabilized by various techniques. The enzymes employed herein can be stabilized by the presence of water-soluble sources of calcium and/or magnesium ions in the finished compositions that provide such ions to the enzymes. In case of aqueous compositions comprising protease, a reversible protease inhibitor, such as a boron compound, can be added to further improve stability.

Catalytic Metal Complexes—Applicants' cleaning compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936; 5,595,967. Such cobalt catalysts are readily prepared by known procedures, such as taught for example in U.S. Pat. Nos. 5,597,936, and 5,595,967.

Compositions herein may also suitably include a transition metal complex of ligands such as bispidones (WO 05/042532 A1) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include, for example, manganese, iron and chromium. Suitable MRLs include 5,12-diethyl-1,5,8,12-tetraazabicyclo[6.6.2]hexadecane.

Suitable transition metal MRLs are readily prepared by known procedures, such as taught for example in WO 00/32601, and U.S. Pat. No. 6,225,464.

Solvents—Suitable solvents include water and other solvents such as lipophilic fluids. Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof.

Processes of Making Compositions

The compositions of the present invention can be formulated into any suitable form and prepared by any process chosen by the formulator, non-limiting examples of which are described in Applicants' examples and in U.S. Pat. No. 4,990,280; U.S. 20030087791A1; U.S. 20030087790A1; U.S. 20050003983A1; U.S. 20040048764A1; U.S. Pat. Nos. 4,762,636; 6,291,412; U.S. 20050227891A1; EP 1070115A2; U.S. Pat. Nos. 5,879,584; 5,691,297; 5,574,005; 5,569,645; 5,565,422; 5,516,448; 5,489,392; 5,486,303 all of which are incorporated herein by reference.

Method of Use

A method of imparting a benefit comprising contacting a fabric comprising a cellulosic material, during a domestic cleaning and/or treatment process, with a composition comprising a xyloglucan conjugate, conjugated at its reducing end with a benefit agent, the balance of said composition comprising an adjunct ingredient. In one aspect, said consumer cleaning and/or treatment composition is selected from a detergent, a fabric softener, a fabric rejuvenation composition, dryer sheet, and/or laundry additive.

A method of imparting a benefit comprising contacting a fabric comprising a cellulosic material, during a domestic cleaning and/or treatment process, with a composition comprising:

a.) from about 0.00001% to about 50% xyloglucan oligosaccharide and/or polysaccharide having the formula:

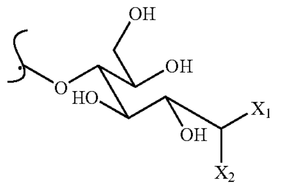

wherein, (i) ∫ represents the remainder of the xyloglucan oligosaccharide or polysaccharide; and (ii) $X_1$ and $X_2$ are each independently

—H;

—$R_1$;

-($L_1$)-$R_1$;

—NH-($L_1$)-$R_1$;

—S-($L_1$)-$R_1$;

—O-($L_1$)-$R_1$;

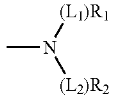

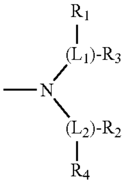

=O wherein a maximum of one of the groups $X_1$ and $X_2$ is —H; and $L_1$ and $L_2$ are optional covalently bonded linker group(s), each being independently selected from:

—C(=O)—;

—C(=S)—;

—$SO_2$—;

-Alk-;

—Ar—;

—Ar-Alk-

-Alk-;

-Alk-Ar—;

-Alk-Ar-Alk-;

—Ar-Alk-Ar—;

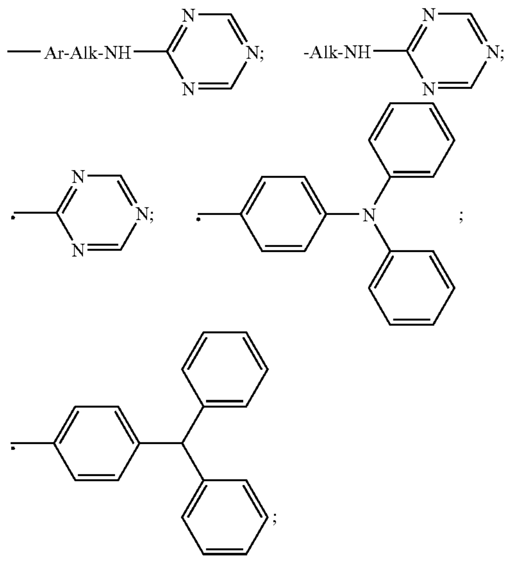

wherein Ar is an aryl or naphthyl ring, which may be further substituted. Alk is an aliphatic group which may be further substituted.

$R_1$, $R_2$, $R_3$, and $R_4$ represent covalently bonded benefit group(s); and b.) the balance of said composition comprising an adjunct ingredient.

In one aspect, said consumer cleaning and/or treatment composition is selected from a detergent, a fabric softener, a fabric rejuvenation composition, dryer sheet, and/or laundry additive.

A method of imparting a benefit agent delivery capability to a consumer cleaning and/or treatment composition, comprising combining said consumer product with from about 0.00001% to about 50% of a xyloglucan conjugate, conjugated at its reducing end with a benefit agent is disclosed.

A method of imparting a benefit agent delivery capability to a consumer cleaning and/or treatment composition, comprising combining said consumer product with from about 0.00001% to about 50% of a xyloglucan conjugate having the formula:

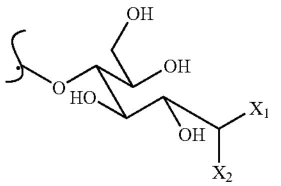

wherein, (i) ʃ represents the remainder of the xyloglucan oligosaccharide or polysaccharide; and (ii) $X_1$ and $X_2$ are each independently

—H;

—$R_1$;

-($L_1$)-$R_1$;

—NH-($L_1$)-$R_1$;

—S-($L_1$)-$R_1$

—O-($L_1$)-$R_1$;

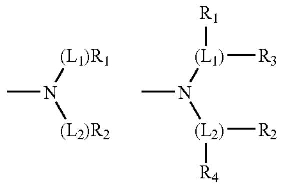

═O wherein a maximum of one of the groups $X_1$ and $X_2$ is —H; and $L_1$ and $L_2$ are optional covalently bonded linker group(s), each being independently selected from:

—C(═O)—;

—C(═S)—;

—$SO_2$—;

-Alk-;

—Ar—;

—Ar-Alk-

-Alk-;

-Alk-Ar—;

-Alk-Ar-Alk-;

—Ar-Alk-Ar—;

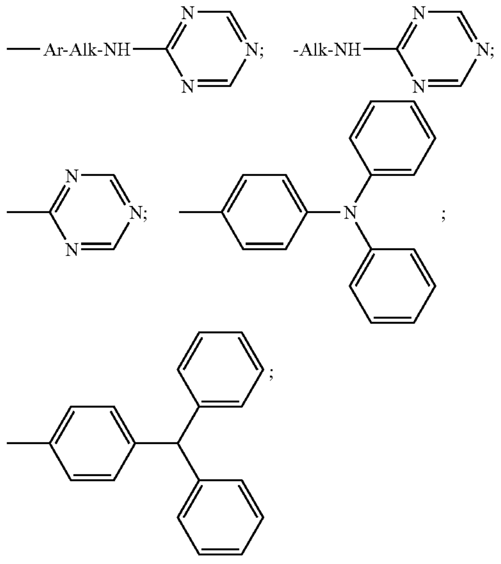

wherein Ar is an aryl or naphthyl ring, which may be further substituted. Alk is an aliphatic group.which may be further substituted.

$R_1$, $R_2$, $R_3$, and $R_4$ represent covalently bonded benefit group(s), is disclosed

EXAMPLES

Unless otherwise indicated, materials can be obtained from Aldrich, P.O. Box 2060, Milwaukee, Wis. 53201, USA.

Examples 1-6

Granular laundry detergent compositions designed for hand washing or top-loading washing machines.

| | 1 (wt %) | 2 (wt %) | 3 (wt %) | 4 (wt %) | 5 (wt %) | 6 (wt %) |
|---|---|---|---|---|---|---|
| Linear alkylbenzenesulfonate | 20 | 22 | 20 | 15 | 20 | 20 |
| $C_{12-14}$ Dimethylhydroxyethyl sammonium chloride | 0.7 | 0.2 | 1 | 0.6 | 0.0 | 0 |
| AE3S | 0.9 | 1 | 0.9 | 0.0 | 0.5 | 0.9 |
| AE7 | 0.0 | 0.0 | 0.0 | 1 | 0.0 | 3 |
| Sodium tripolyphosphate | 5 | 0.0 | 4 | 9 | 2 | 0.0 |
| Zeolite A | 0.0 | 0.0 | 0.0 | 1 | 4 | 1 |
| 1.6R Silicate ($SiO_2$:$Na_2O$ at ratio 1.6:1) | 7 | 12 | 2 | 3 | 3 | 5 |
| Sodium Carbonate | 25 | 9.0 | 25 | 17 | 18 | 19 |
| Polyacrylate MW 4500 | 1 | 0.6 | 1 | 1 | 1.5 | 1 |
| Carboxy Methyl Cellulose | 1 | 0.3 | 1 | 1 | 1 | 1 |
| Savinase ® (32.89 mg active/g) | 0.1 | 0.1 | 0.1 | 0.1 | 0.1 | 0.1 |
| Natalase ® (8.65 mg active/g) | 0.1 | 0.0 | 0.1 | 0.0 | 0.1 | 0.1 |
| Lipex ® (18 mg active/g) | 0.03 | 0.07 | 0.3 | 0.1 | 0.07 | 0.4 |
| Fluorescent Brightener 1 | 0.06 | 0.0 | 0.06 | 0.18 | 0.06 | 0.06 |
| Fluorescent Brightener 2 | 0.1 | 0.06 | 0.1 | 0.0 | 0.1 | 0.1 |
| DTPA | 0.6 | 0.8 | 0.6 | 0.25 | 0.6 | 0.6 |
| $MgSO_4$ | 1 | 1 | 1 | 0.5 | 1 | 1 |
| Sodium Percarbonate | 0.0 | 5.2 | 0.1 | 0.0 | 0.0 | 0.0 |
| Sodium Perborate Monohydrate | 4.4 | 0.0 | 3.85 | 2.09 | 0.78 | 3.63 |
| NOBS | 1.9 | 0.0 | 1.66 | 0.0 | 0.33 | 0.75 |
| TAED | 0.58 | 1.2 | 0.51 | 0.0 | 0.015 | 0.28 |
| Sulphonated zinc phthalocyanine | 0.0030 | 0.0 | 0.0012 | 0.0030 | 0.0021 | 0.0 |
| Direct Violet 9 | 0.0 | 0.0 | 0.0003 | 0.0005 | 0.0003 | 0.0 |
| Xyloglucan conjugate with C.I. Reactive Blue 4 dye* | 0.02 | 0.2 | 0.3 | 0.2 | 0.09 | 0.2 |
| Sulfate/Moisture** | | | | | | |

**Balance to 100%

Examples 7-12

Granular laundry detergent compositions designed for front-loading automatic washing machines.

| | 7 (wt %) | 8 (wt %) | 9 (wt %) | 10 (wt %) | 11 (wt %) | 12 (wt %) |
|---|---|---|---|---|---|---|
| Linear alkylbenzenesulfonate | 8 | 7.1 | 7 | 6.5 | 7.5 | 7.5 |
| AE3S | 0 | 4.8 | 0 | 5.2 | 4 | 4 |
| Alkylsulfate | 1 | 0 | 1 | 0 | 0 | 0 |
| AE7 | 2.2 | 0 | 3.2 | 0 | 0 | 0 |
| $C_{10-12}$ Dimethyl hydroxyethylammonium chloride | 0.75 | 0.94 | 0.98 | 0.98 | 0 | 0 |
| Crystalline layered silicate (δ-$Na_2Si_2O_5$) | 4.1 | 0 | 4.8 | 0 | 0 | 0 |
| Zeolite A | 5 | 0 | 5 | 0 | 2 | 2 |
| Citric Acid | 3 | 5 | 3 | 4 | 2.5 | 3 |
| Sodium Carbonate | 15 | 20 | 14 | 20 | 23 | 23 |
| Silicate 2R ($SiO_2$:$Na_2O$ at ratio 2:1) | 0.08 | 0 | 0.11 | 0 | 0 | 0 |
| Soil release agent | 0.75 | 0.72 | 0.71 | 0.72 | 0 | 0 |
| Acrylic Acid/Maleic Acid Copolymer | 1.1 | 3.7 | 1.0 | 3.7 | 2.6 | 3.8 |
| Carboxymethylcellulose | 0.15 | 1.4 | 0.2 | 1.4 | 1 | 0.5 |
| Protease (84 mg active/g) | 0.2 | 0.2 | 0.3 | 0.15 | 0.12 | 0.13 |
| Lipex ® (18.00 mg active/g) | 0.05 | 0.15 | 0.1 | 0 | 0 | 0 |
| Natalase ® (8.65 mg active/g) | 0.1 | 0.2 | 0 | 0 | 0.15 | 0.15 |
| Celluclean ™ (15.6 mg active/g) | 0 | 0 | 0 | 0 | 0.1 | 0.1 |
| TAED | 3.6 | 4.0 | 3.6 | 4.0 | 2.2 | 1.4 |
| Percarbonate | 13 | 13.2 | 13 | 13.2 | 16 | 14 |
| Na salt of Ethylenediamine-N,N'-disuccinic acid, (S,S) isomer (EDDS) | 0.2 | 0.2 | 0.2 | 0.2 | 0.2 | 0.2 |
| Hydroxyethane di phosphonate (HEDP) | 0.2 | 0.2 | 0.2 | 0.2 | 0.2 | 0.2 |
| $MgSO_4$ | 0.42 | 0.42 | 0.42 | 0.42 | 0.4 | 0.4 |
| Perfume | 0.5 | 0.6 | 0.5 | 0.6 | 0.6 | 0.6 |
| Suds suppressor agglomerate | 0.05 | 0.1 | 0.05 | 0.1 | 0.06 | 0.05 |
| Soap | 0.45 | 0.45 | 0.45 | 0.45 | 0 | 0 |

-continued

| | 7 (wt %) | 8 (wt %) | 9 (wt %) | 10 (wt %) | 11 (wt %) | 12 (wt %) |
|---|---|---|---|---|---|---|
| Sulphonated zinc phthalocyanine (active) | 0.0007 | 0.0012 | 0.0007 | 0 | 0 | 0 |
| Direct Violet 9 (active) | 0 | 0 | 0.0001 | 0.0001 | 0 | 0 |
| Xyloglucan conjugate with C.I. Reactive Blue 4 dye* | 0.1 | 0.07 | 0.1 | 0.03 | 0.06 | 0.3 |
| Sulfate/Water & Miscellaneous** | | | | | | |

Any of the above compositions is used to launder fabrics at a concentration of 7000 to 10000 ppm in water, 20-90° C., and a 5:1 water:cloth ratio. The typical pH is about 10.
**Balance to 100%

Examples 13-16

Heavy Duty Liquid Laundry Detergent Compositions

| | 13 (wt %) | 14 (wt %) | 15 (wt %) | 16 (wt %) |
|---|---|---|---|---|
| AES $C_{12-15}$ alkyl ethoxy (1.8) sulfate | 11 | 10 | 4 | 6.32 |
| Linear alkyl benzene sulfonate | 1.4 | 4 | 8 | 3.3 |
| HSAS | 3 | 5.1 | 3 | 0 |
| Sodium formate | 1.6 | 0.09 | 1.2 | 0.04 |
| Sodium hydroxide | 2.3 | 3.8 | 1.7 | 1.9 |
| Monoethanolamine | 1.4 | 1.49 | 1.0 | 0.7 |
| Diethylene glycol | 5.5 | 0.0 | 4.1 | 0.0 |
| Nonionic 23,9 | 0.4 | 0.6 | 0.3 | 0.3 |
| Nonionic 24,7 | 0 | 0 | 0 | 0 |
| Chelant | 0.15 | 0.15 | 0.11 | 0.07 |
| Citric Acid | 2.5 | 3.96 | 1.88 | 1.98 |
| $C_{12-14}$ dimethyl Amine Oxide | 0.3 | 0.73 | 0.23 | 0.37 |
| $C_{12-18}$ Fatty Acid | 0.8 | 1.9 | 0.6 | 0.99 |
| Borax | 1.43 | 1.5 | 1.1 | 0.75 |
| Ethanol | 1.54 | 1.77 | 1.15 | 0.89 |
| Ethoxylated ($EO_{15}$) tetraethylene pentaimine[1] | 0.3 | 0.33 | 0.23 | 0.17 |
| Ethoxylated hexamethylene diamine[2] | 0.8 | 0.81 | 0.6 | 0.4 |
| 1,2-Propanediol | 0.0 | 6.6 | 0.0 | 3.3 |
| Protease (40.6 mg active/g) | 0.8 | 0.6 | 0.7 | 0.9 |
| Mannaway ® (25 mg active/g) | 0.07 | 0.05 | 0.045 | 0.06 |
| Natalase ® (29 mg active/g) | 0 | 0.2 | 0.1 | 0.15 |
| Lipex ® (18 mg active/g) | 0.4 | 0.2 | 0.3 | 0.1 |
| Liquitint ® Violet CT (active) | 0.006 | 0.002 | 0 | 0 |
| Xyloglucan conjugate with C.I. Reactive Blue 4 dye* | 0.03 | 0.02 | 0.1 | 0.2 |
| Water, perfume, dyes & other components** | | | | |

**Balance to 100%

Examples 17-18

Liquid Laundry Detergent Designed to Clean and Rejuvenate Black Fabrics

| | 17 (wt %) | 18 (wt %) |
|---|---|---|
| AES $C_{12-15}$ alkyl ethoxy (1.8) sulfate | 5 | 10 |
| Linear alkyl benzene sulfonate | 1.4 | 4 |
| Sodium formate | 1.6 | 0.09 |
| Sodium hydroxide | 2.3 | 3.8 |
| Monoethanolamine | 1.4 | 1.49 |
| Diethylene glycol | 5.5 | 0.0 |
| Nonionic 23,9 | 0.4 | 0.6 |
| Chelant | 0.15 | 0.15 |
| Citric Acid | 2.5 | 3.96 |
| $C_{12-14}$ dimethyl Amine Oxide | 0.3 | 0.73 |
| $C_{12-18}$ Fatty Acid | 0.8 | 1.9 |
| Borax | 1.43 | 1.5 |
| Ethanol | 1.54 | 1.77 |
| Ethoxylated ($EO_{15}$) tetraethylene pentaimine[1] | 0.3 | 0.33 |
| Ethoxylated hexamethylene diamine[2] | 0.8 | 0.81 |
| 1,2-Propanediol | 0.0 | 6.6 |
| Protease (40.6 mg active/g) | 0.8 | 0.6 |
| Carezyme ® (25 mg active/g) | 0.1 | 0.13 |
| Natalase ® (29 mg active/g) | 0 | 0.2 |
| Xyloglucan conjugate with C.I. Reactive Black 5 dye* | 0.3 | 0.5 |
| Water, perfume, dyes & other components** | | |

**Balance to 100%

Raw Materials and Notes For Composition Examples 1-18

Linear alkylbenzenesulfonate having an average aliphatic carbon chain length $C_{11}$-$C_{12}$ supplied by Stepan, Northfield, Ill., USA $C_{12-14}$ Dimethylhydroxyethyl ammonium chloride, supplied by Clariant GmbH, Sulzbach, Germany AE3S is $C_{12-15}$ alkyl ethoxy(3)sulfate supplied by Stepan, Northfield, Ill., USA AE7 is $C_{12-15}$ alcohol ethoxylate, with an average degree of ethoxylation of 7, supplied by Huntsman, Salt Lake City, Utah, USA Sodium tripolyphosphate is supplied by Rhodia, Paris, France Zeolite A is supplied by Industrial Zeolite (UK) Ltd, Grays, Essex, UK 1.6R Silicate is supplied by Koma, Nestemica, Czech Republic Sodium Carbonate is supplied by Solvay, Houston, Tex., USA Polyacrylate MW 4500 is supplied by BASF, Ludwigshafen, Germany Carboxy Methyl Cellulose is Finnfix® BDA supplied by CP Kelco, Arnhem, Netherlands Suitable chelants are, for example, diethylenetetraamine pentaacetic acid (DTPA) supplied by Dow Chemical, Midland, Mich., USA or Hydroxyethane di phosphonate (HEDP) supplied by Solutia, St Louis, Mo., USA Lipex®, Carezyme®, Mannaway®, Savinase®, and Celluclean™ are supplied by Novozyme A/S, Bagsvaerd, Denmark Protease (examples 7-12) described in U.S. Pat. No. 6,312,936 B1 supplied by Genencor International, Palo Alto, Calif., USA Protease (examples 13-18) described in U.S. Pat. No. 4,760,025 is supplied by Genencor International, Palo Alto, Calif., USA Fluorescent Brightener 1 is Tinopal® AMS, Fluorescent Brightener 2 is Tinopal® CBS-X, Sulphonated zinc phthalocyanine and Direct Violet 9 is Pergasol® Violet BN-Z all supplied by Ciba Specialty Chemicals, Basel, Switzerland Sodium percarbonate supplied by Solvay, Houston, Tex., USA Sodium perborate is supplied by Degussa, Hanau, Germany NOBS is sodium nonanoyloxybenzenesulfonate, supplied by Eastman, Batesville, Ark., USA TAED is tetraacetylethylenediamine, supplied under the Peractive® brand name by Clariant GmbH, Sulzbach, Germany Soil release agent is Repel-o-tex® PF, supplied by Rhodia, Paris, France Acrylic Acid/Maleic Acid Copolymer is molecular weight 70,000 and acrylate:maleate ratio 70:30, supplied by BASF, Ludwigshafen, Germany Na salt of Ethylenediamine-N,N'-disuccinic acid, (S,S) isomer (EDDS) is supplied by Octel, Ellesmere Port, UK Hydroxyethane di phosphonate (HEDP) is supplied by Dow Chemical, Midland, Mich., USA Suds suppressor agglomerate is supplied by Dow Corning, Midland, Mich., USA HSAS is mid-branched alkyl sulfate as disclosed in U.S. Pat. No. 6,020,303 and U.S. Pat. No. 6,060,443

$C_{12-14}$ dimethyl Amine Oxide is supplied by Procter & Gamble Chemicals, Cincinnati, Ohio, USA Liquitint® Violet CT is supplied by Milliken, Spartanburg, S.C., USA)

[1]as described in U.S. Pat. No. 4,597,898 . . .

[2]available under the tradename LUTENSIT® from BASF and such as those described in WO 01/05874

Xyloglucan conjugate with C.I. Reactive Blue 4 dye was prepared as described in USPA 2006/0242770 A1, example 10, followed by purification on a C18 column and lyophilisation

*Or other xyloglucan conjugate according to the present invention

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising a xyloglucan conjugate, conjugated at its reducing end with a covalently bonded benefit agent, and, based on total composition weight, from about 0.1% to about 60% of a surfactant, wherein said benefit agent is selected from the group consisting of perfumes, perfume particles, fluorescent brighteners, oil repellent agents, water repellent agents, soil release agents, soil repellent agents, dyes, fabric renewing dyes, hueing dyes, dye intermediates, dye fixatives, lubricants, fabric softeners, photofading inhibitors, antiwrinkle/ironing agents, shape retention agents, UV absorbers, sunscreens, antioxidants, crease resistant agents, antimicrobial agents, skin benefit agents, anti-fungal agents, insect repellents, photobleaches, photoinitiators, sensates, enzyme inhibitors, bleach catalysts, odor neutralizing agents, pheromones and mixtures thereof.

2. A composition according to claim 1 comprising:

a.) from about 0.00001% to about 50% xyloglucan oligosaccharide and/or polysaccharide having the formula:

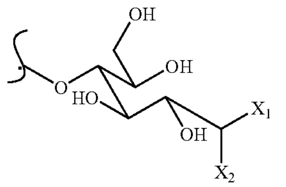

wherein, (i) ʃ represents the remainder of the xyloglucan oligosaccharide or polysaccharide; and (ii) $X_1$ and $X_2$ are each independently

—H;

—$R_1$;

-($L_1$)-$R_1$;

—NH-($L_1$)-$R_1$;

—S-($L_1$)-$R_1$

—O-($L_1$)-$R_1$;

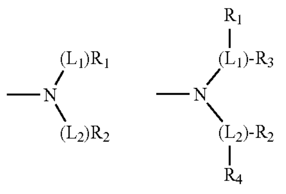

=O wherein a maximum of one of the groups $X_1$ and $X_2$ is —H; and $L_1$ and $L_2$ are optional covalently bonded linker group(s), each being independently selected from:

—C(=O)—;

—C(=S)—;

—$SO_2$—;

-Alk-;
—Ar—;
—Ar-Alk-
-Alk-;
-Alk-Ar—;
-Alk-Ar-Alk-;
—Ar-Alk-Ar—;

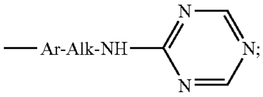

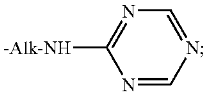

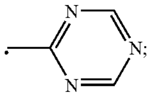

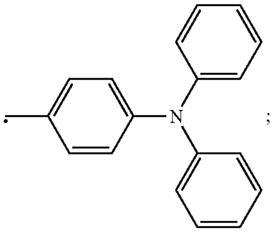

;

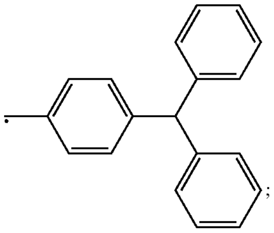

wherein Ar is an aryl or naphthyl ring, which may be further substituted, Alk is an aliphatic group which may be further substituted;

$R_1$, $R_2$, $R_3$, and $R_4$ represent covalently bonded benefit group(s); and b.) the balance of said composition comprising an adjunct ingredient.

3. A method of imparting a benefit comprising contacting a fabric comprising a cellulosic material, during a domestic cleaning and/or treatment process, with the composition of claim 1.

4. A method of imparting a benefit comprising contacting a fabric comprising a cellulosic material, during a domestic cleaning and/or treatment process, with the composition of claim 2.

5. A method of imparting a benefit agent delivery capability to a consumer cleaning and/or treatment composition containing from about 0.1% to about 60% of a surfactant, comprising combining said consumer product with from about 0.00001% to about 50% of a xyloglucan conjugate, conjugated at its reducing end with a covalently bonded benefit agent selected from the group consisting of perfumes, perfume particles, fluorescent brighteners, oil repellent agents, water repellent agents, soil release agents, soil repellent agents, dyes, fabric renewing dyes, hueing dyes, dye intermediates, dye fixatives, lubricants, fabric softeners, photofading inhibitors, antiwrinkle/ironing agents, shape retention agents, UV absorbers, sunscreens, antioxidants, crease resistant agents, antimicrobial agents, skin benefit agents, antifungal agents, insect repellents, photobleaches, photoinitiators, sensates, enzyme inhibitors, bleach catalysts, odor neutralizing agents, pheromones and mixtures thereof.

6. A method of imparting a benefit agent delivery capability to a consumer cleaning and/or treatment composition containing from about 0.1% to about 60% of a surfactant, comprising combining said consumer product with from about 0.00001% to about 50% of a xyloglucan conjugate having the formula:

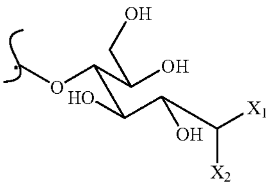

wherein, (i) ∫ represents the remainder of the xyloglucan oligosaccharide or polysaccharide; and (ii) $X_1$ and $X_2$ are each independently
—H;
—$R_1$;
-($L_1$)-$R_1$;
—NH-($L_1$)-$R_1$;
—S-($L_1$)-$R_1$
—O-($L_1$)-$R_1$;

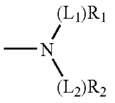

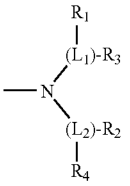

=O wherein a maximum of one of the groups $X_1$ and $X_2$ is —H; and $L_1$ and $L_2$ are optional covalently bonded linker group(s), each being independently selected from:
—C(=O)—;
—C(=S)—;
—$SO_2$—;
-Alk-;
—Ar—;
—Ar-Alk-
-Alk-;
-Alk-Ar—;
-Alk-Ar-Alk-;
—Ar-Alk-Ar—;

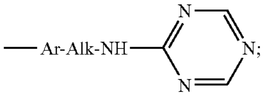

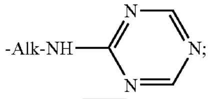

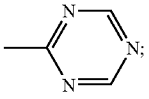

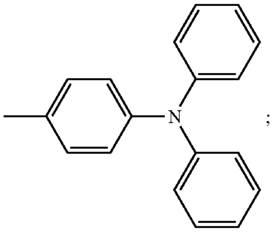

;

-continued

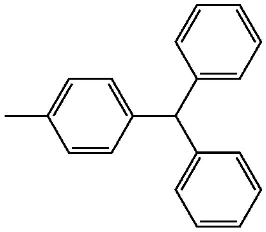

;

wherein Ar is an aryl or naphthyl ring, which may be further substituted, Alk is an aliphatic group which may be further substituted;

$R_1$, $R_2$, $R_3$, and $R_4$ represent covalently bonded benefit group(s) selected from the group consisting of perfumes, perfume particles, fluorescent brighteners, oil repellent agents, water repellent agents, soil release agents, soil repellent agents, dyes, fabric renewing dyes, hueing dyes, dye intermediates, dye fixatives, lubricants, fabric softeners, photofading inhibitors, anti-wrinkle/ironing agents, shape retention agents, UV absorbers, sunscreens, antioxidants, crease resistant agents, antimicrobial agents, skin benefit agents, antifungal agents, insect repellents, photobleaches, photoinitiators, sensates, enzyme inhibitors, bleach catalysts, odor neutralizing agents, pheromones and mixtures thereof.

7. The method of claim 5, wherein said consumer cleaning and/or treatment composition is selected from a detergent, a fabric softener, a fabric rejuvenation composition, dryer sheet, and/or laundry additive.

8. The method of claim 6, wherein said consumer cleaning and/or treatment composition is selected from a detergent, a fabric softener, a fabric rejuvenation composition, dryer sheet, and/or laundry additive.

* * * * *